(12) United States Patent
Kleen

(10) Patent No.: US 7,000,609 B2
(45) Date of Patent: Feb. 21, 2006

(54) HOLDING DEVICE FOR A MEDICAL BREATHING TUBE

(75) Inventor: Martin Kleen, Neunkirchen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/957,437

(22) Filed: Oct. 1, 2004

(65) Prior Publication Data

US 2005/0072424 A1 Apr. 7, 2005

(30) Foreign Application Priority Data

Oct. 2, 2003 (DE) ............................. 103 46 014

(51) Int. Cl.
*A62B 9/04* (2006.01)

(52) U.S. Cl. ...................... 128/202.27; 24/527; 248/73

(58) Field of Classification Search ................
128/207.14–207.18, DIG. 26, 911, 912,
128/202.27, DIG. 24, 200.24, 200.26; 248/49,
248/68.1, 74.4, 225.31, 230, 231.2, 68 CB;
24/1, 3.11, 527, 3.12, 115 R, 129 R, 130,
24/115, 545, 546, 563, 570, 463; 604/179,
604/93.01, 104, 174, 264, 523, 910; 285/373,
285/419; 174/155–157; 600/201, 215, 226–228,
600/231, 232, 234, 235; 606/190, 191, 198
See application file for complete search history.

(56) References Cited

U.S. PATENT DOCUMENTS

| | | | | | |
|---|---|---|---|---|---|
| 2,963,539 | A | * | 12/1960 | Hynes | 174/138 J |
| 3,894,706 | A | * | 7/1975 | Mizusawa | 248/68.1 |
| 4,273,465 | A | * | 6/1981 | Schoen | 403/391 |
| 4,936,530 | A | * | 6/1990 | Wollar | 248/71 |
| 5,333,826 | A | * | 8/1994 | Lai | 248/229.14 |
| 5,833,191 | A | * | 11/1998 | Gennep | 248/288.51 |
| 6,308,921 | B1 | * | 10/2001 | Borzucki | 248/68.1 |
| 6,783,520 | B1 | * | 8/2004 | Candray et al. | 604/500 |
| 2003/0034030 | A1 | | 2/2003 | Carlucci et al. | |

* cited by examiner

Primary Examiner—Henry Bennett
Assistant Examiner—Shumaya B. Ali

(57) ABSTRACT

A retaining device (1) for ventilation tubes (5) has two gripping jaws (2, 3), which can be locked into each other by means of a rack (11). The lower gripping jaw (3) can be attached to a stretcher via a bracket (6).

9 Claims, 3 Drawing Sheets

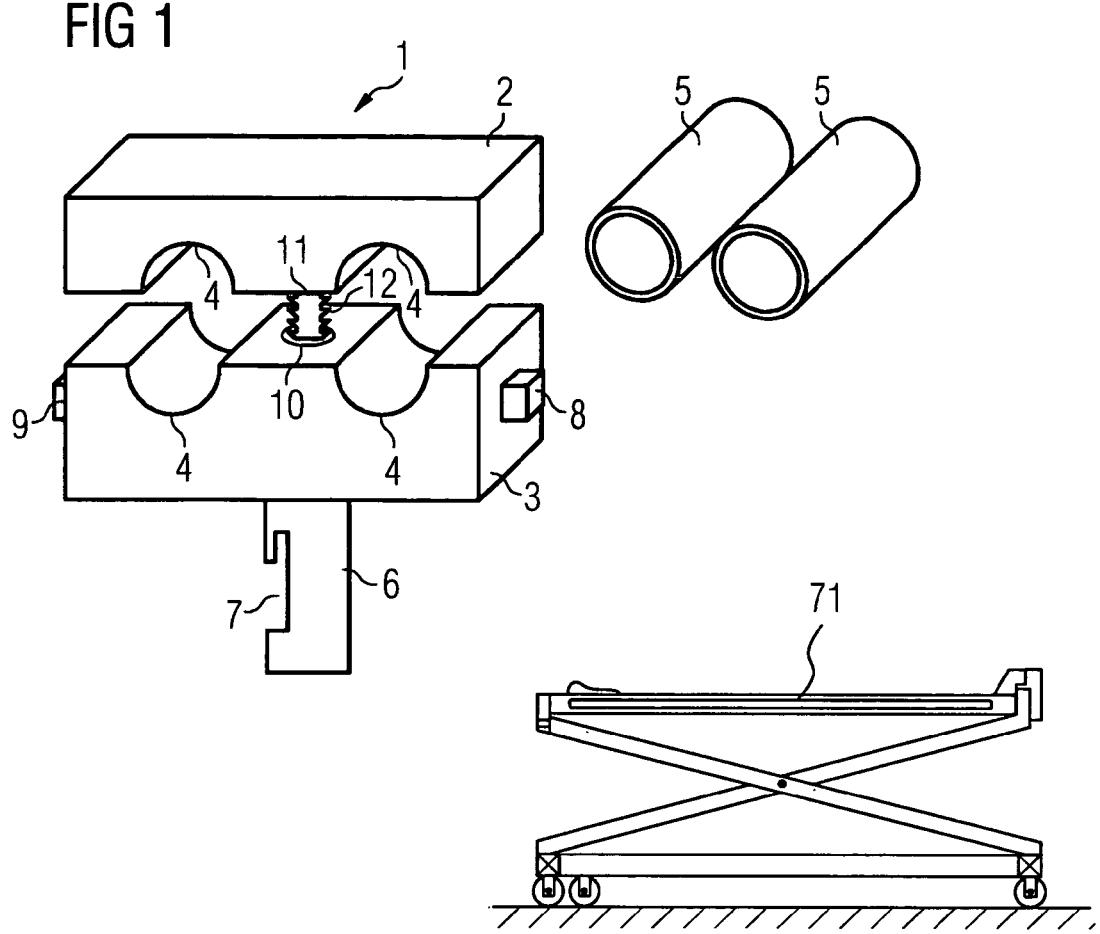
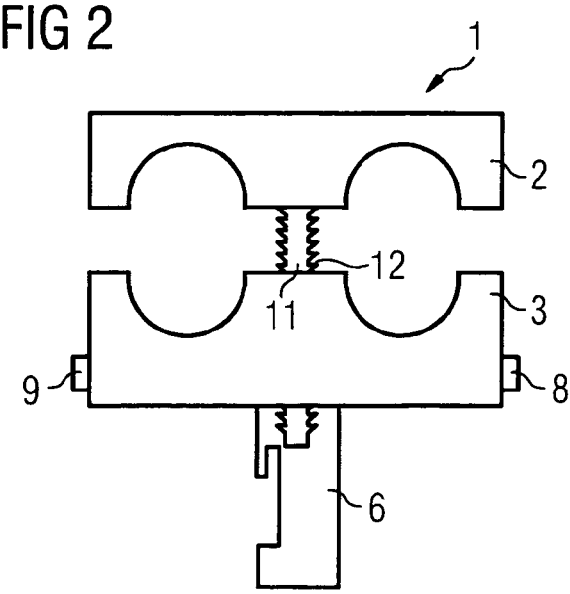

HOLDING DEVICE FOR A MEDICAL BREATHING TUBE

CROSS REFERENCE TO RELATED APPLICATIONS

This application claims priority to the German application No. 10346014.4, filed Oct. 2, 2003 and which is incorporated by reference herein in its entirety.

The invention relates to holding device for a medical breathing tube with a clamp surrounding the breathing tube and held in a predefined position in relation to the body of the patient. In the following, the holding device will also be referred to as a or the retaining device, and the breathing tube will also be referred to as a or the ventilation tube.

BACKGROUND OF THE INVENTION

Such a retaining device is known from US 2003/0034030 A1. The known device has a headband, which can be placed on the head of a patient and on which clips are configured, into which the ventilation tube can be inserted.

One advantage of the known retaining device is that the ventilation tubes also move with the movement of the head of the patient. Using a headband ensures that the support is held in a more comfortable manner on the head of the patient. In particular blood circulation is not impaired by it. In conjunction with ventilation tubes inserted through the nose, the known retaining device ensures that ventilation tubes are held relatively securely on the head of the patient.

SUMMARY OF THE INVENTION

One disadvantage of the known retaining device is that it cannot be used for ventilation tubes, which are deployed in the case of general anesthesia. Such ventilation tubes serve to connect a patient to a ventilator by means of an endotracheal tube, a mask or a laryngeal mask. Ventilation tubes are generally made of silicon, are up to several meters long and have relatively thick walls. Ventilation tubes therefore have a relatively large mass of around one to three kilograms. Unless counter-measures are taken, this large mass acts on the endotracheal tube and can cause dislocation of the endotracheal tube with potentially life-threatening consequences. It is therefore important to keep the ventilation tubes as still as possible in their spatial position in relation to the patient. It is frequently the case that the ventilator generally cannot be moved, whereas the stretcher on which the patient is lying moves to a significant degree. The stretchers, which can for example be operating tables or X-ray examination tables, are for example rotated, tipped, raised or lowered. These movements give rise to the risk of dislocation of the endotracheal tube or mask or laryngeal mask, which can in extreme cases interrupt ventilation. If this is not noticed, the patient can suffer injury.

Based on the prior art, an object of the invention is to create a retaining device for ventilation tubes, which maintains the relative position of the ventilation tubes in relation to the body of the patient, even when the stretcher moves to a significant degree in relation to the ventilator.

This object is achieved according to the invention by the claims. Advantageous embodiments and developments are specified in the dependent claims.

The retaining device according to the invention has two gripping jaws, which can be locked into each other and between which the ventilation tube can be clamped. At least one of the gripping jaws can also be attached to the stretcher by means of an attachment device.

The attachment device allows the gripping jaws to be fixed to the stretcher. The ends of the ventilation tubes clamped between the jaws therefore do not move, even if the stretcher is moved to a significant degree in relation to the ventilator. There is therefore no risk of dislocation of the ventilation tubes with the retaining device according to the invention.

In a preferred embodiment, a projection with undercuts is provided on one of the gripping jaws and can be inserted into a recess located on the other gripping jaw that is provided with the locking device. This arrangement offers the advantage that when the projection is inserted into the recess, the gripping jaws are aligned.

In a further preferred embodiment the projection that can be inserted into the recess of the gripping jaw has regular undercuts, into which the locking device can be locked. In this way the distance between the gripping jaws can be adjusted to the respective diameter of the ventilation tube.

The undercuts on the projection are preferably configured so that the locking device of the gripping jaw, into which the projection is inserted, can be subjected to pressure. The projection can thereby be pushed into the recess as far as is necessary for the gripping jaw to be positioned securely on the ventilation tube.

The locking device preferably has a locking bar, which is held in one of the undercuts on the projection by means of a spring. If the spring force applied by the spring is offset by a release mechanism activated by the operator, the locking bar can slide out of the undercut and release the associated gripping jaw. Such a retaining device can advantageously be released again at any time.

In a further preferred embodiment at least two locking bars are provided, which engage in the undercuts of the projection and are held there by springs, which can each be neutralized by an assigned release mechanism. This embodiment prevents the retaining device being released by unintentional activation of the release device.

In a further preferred embodiment the recess provided in one of the two gripping jaws to hold the projection is configured as a blind hollow. This is to prevent the undercuts of the projection accidentally trapping the operator's hand when the gripping jaws are released.

BRIEF DESCRIPTION OF THE DRAWINGS

Further details and advantages of the invention will emerge from the description below, in which exemplary embodiments of the invention are described in detail with reference to the drawing, in which:

FIG. 1 shows a perspective view of the retaining device;

FIG. 2 shows a cross-section through the retaining device from FIG. 1;

DETAILED DESCRIPTION OF THE INVENTION

Figure 3:
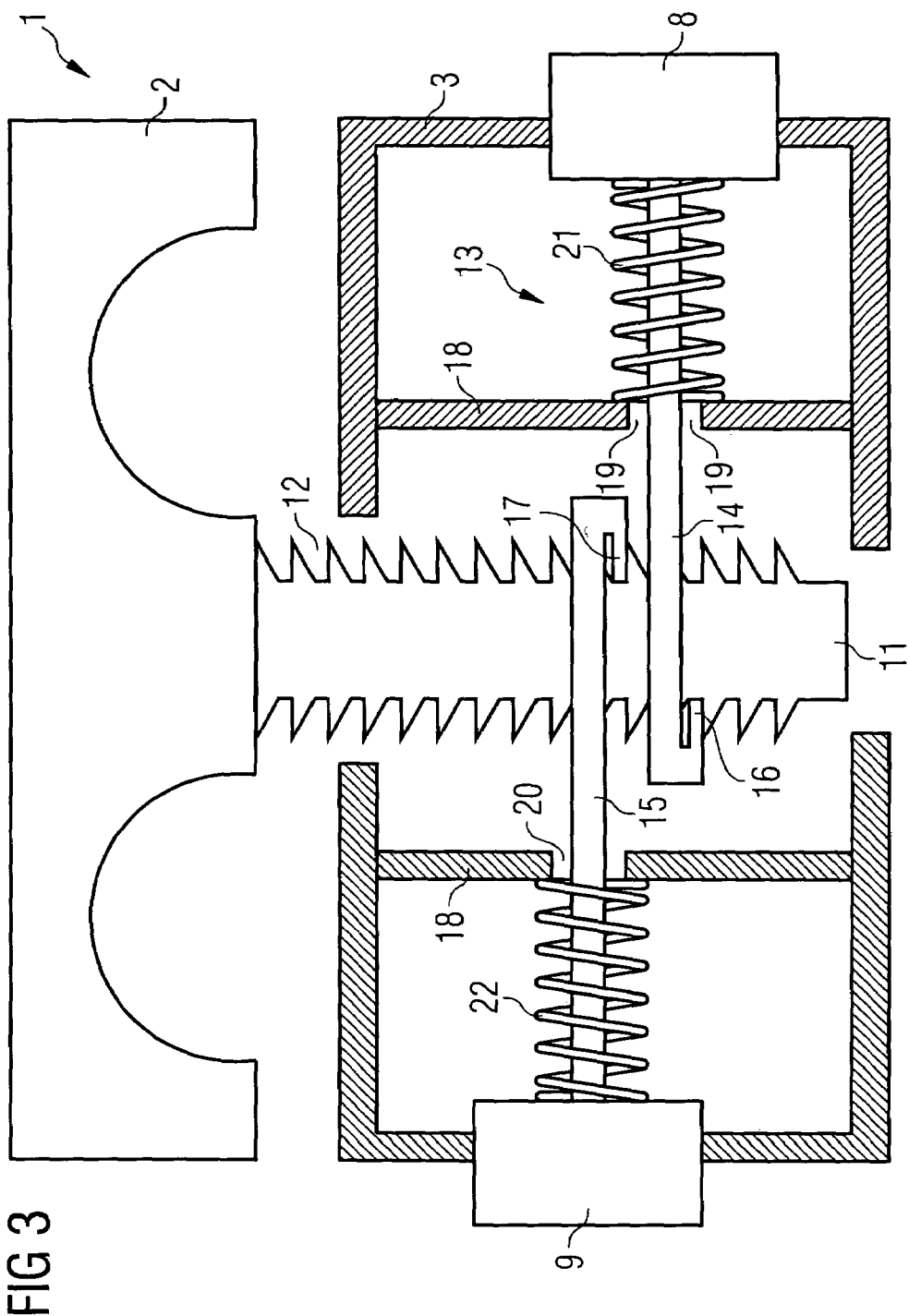
FIG. 3 shows a further cross-section through the retaining device from FIGS. 1 and 2.

FIG. 1 shows a retaining device 1 having two gripping jaws 2 and 3. The gripping jaws 2 and 3 each have recesses 4, each of which serves to hold a ventilation tube 5. The lower gripping jaw 3 is also attached to a bracket 6, on which a sealed retaining groove 7 is configured to attach the bracket 6 to a stretcher 71. The stretcher 71 can for example be an operating table or an X-ray examination table.

Operating buttons 8 and 9 are also provided on the lower gripping jaw 3, by means of which a locking device configured inside the lower gripping jaw 3 can be activated. This locking device is described in detail below.

The lower gripping jaw 3 also has an opening 10, into which a rack 11 can be inserted. The rack 11 has saw-tooth undercuts 12.

To fit the ventilation tubes 5 in the retaining device 1 the rack 11 attached to the upper gripping jaw 2 is inserted into the lower gripping jaw 3 and then the ventilation tubes 5 are inserted into the recesses 4. Pressing down the upper gripping jaw 2 reduces the distance between the upper gripping jaw 2 and the lower gripping jaw 3 such that the ventilation tubes 5 are clamped between the upper gripping jaw 2 and the lower gripping jaw 3. The rack 11 is thereby locked in the lower gripping jaw 3.

To release the gripping jaws 2 and 3 the operating buttons 8 and 9 are activated at the same time. This releases the rack 11 of the upper gripping jaw 2 from the lower gripping jaw 3 and the lower gripping jaw 3 and the upper gripping jaw 2 can be pulled apart, so that the ventilation tubes 5 can be taken out of the recesses 4.

FIG. 2 shows a first cross-section through the retaining device 1 from FIG. 1. It can be seen from FIG. 2 that the rack 11 already projects over the lower gripping jaw 3, when the lower gripping jaw 3 and the upper gripping jaw 2 are at a distance from each other. The bracket 6 is preferably configured as hollow or has a hole, so that the end of the rack 11 projecting from the lower gripping jaw 3 is covered by the bracket 6. This is to prevent the operator's hand catching in the undercuts 12 and being trapped between the rack 11 and the lower gripping jaw 3 when the gripping jaws 2 and 3 are released.

Figure 4:
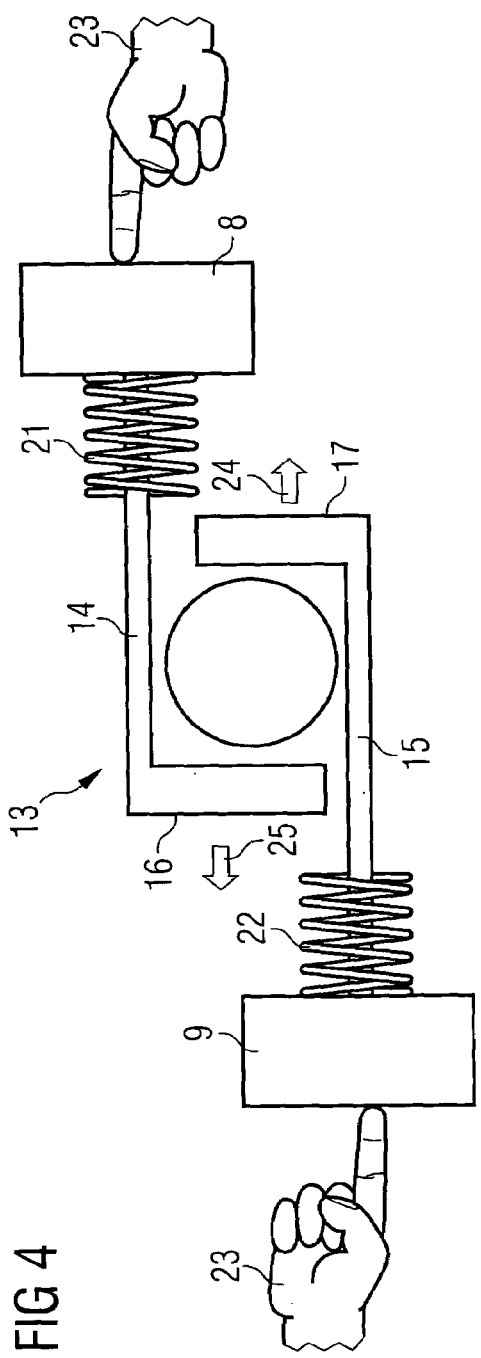
FIG. 4 shows a diagram of the locking device when activated.

FIG. 3 shows a further cross-section through the retaining device 1, showing an exemplary embodiment of a locking device 13 arranged in the lower gripping jaw 3. It can be seen in FIG. 3 that the operating buttons 8 and 9 are each attached to a locking bar 14 and 15. As can also be seen in FIGS. 4 and 5, the locking bars 14 and 15 enclose the rack 11 and extend with retaining segments 16 and 17 running in a transverse direction into the undercuts 12 of the rack 11.

As shown in FIG. 3, a supporting wall 18 enclosing the rack 11 is configured in the lower gripping jaw 3. Openings 19 and 20 are provided in the supporting wall 18, through which the locking bars 14 and 15 are guided to the rack 11. Between the supporting wall 18 and the operating buttons 8 and 9 the locking bars 14 and 15 are surrounded by helical compression springs 21 and 22, the end of which nearest to the rack 11 is in contact with the supporting wall and the opposite end of which is in contact with the operating button 8 and 9. The helical compression springs 21 and 22 push the operating buttons 8 and 9 outwards and pull the retaining segments 16 and 17 into the undercuts 12 of the rack 11.

Figure 5:
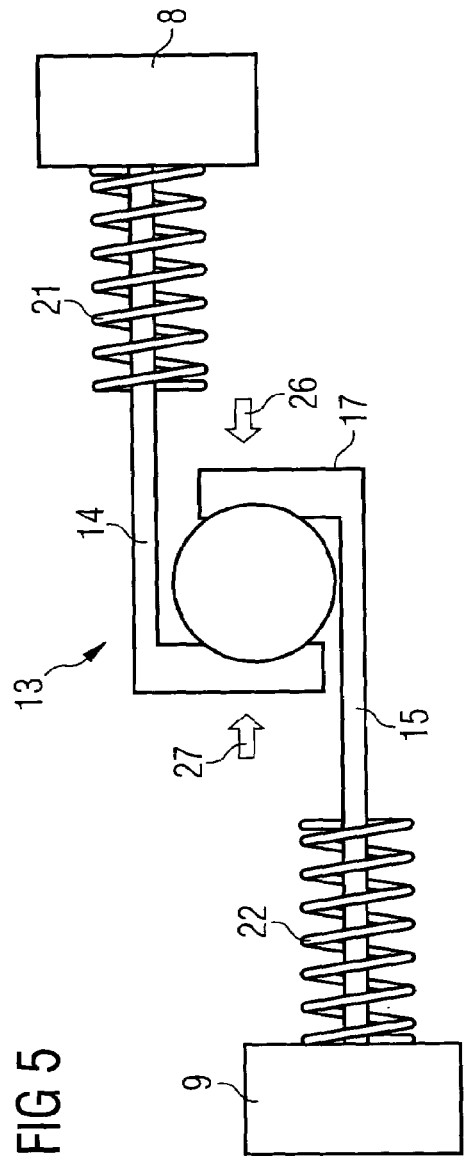
FIG. 5 shows a diagram of the locking device when locked.

To release the locking device 13 the operating buttons 8 and 9 are pushed by the hands 23 of an operator at the same time, so that the retaining segments 16 and 17 move in the direction of arrows 24 and 25. This releases the rack 11 and the upper gripping jaw 2 can be removed from the lower gripping jaw 3. Once the operating buttons 8 and 9 have been released, the retaining segments 16 and 17 slide back as shown in FIG. 5 in the direction of arrows 26 and 27 into the hollows 12 of the rack 11. In the non-operational state the retaining segments 16 and 17 engage as shown in FIG. 5 in the undercuts 12 of the rack 11.

The undercuts 12 on the rack 11 are advantageously configured such that the retaining segments 16 and 17 are subject to pressure when the rack 11 is inserted. The retaining segments 16 and 17 then snap into the undercuts 12 of the rack 11 and ensure that the rack 11 is securely positioned in the opening 10.

To facilitate insertion of the rack 11 into the opening 10, the opening 10 can be configured in a tapered manner on the side facing the upper gripping jaw 2. Otherwise the opening 10 should be dimensioned such that the rack 11 fits correctly in the lower gripping jaw 3.

To facilitate release of the gripping jaws 2 and 3, a compression spring (not shown in the drawing) can be provided in the bracket 6 to push the rack 11 upward. However generally the elasticity of the ventilation tubes 5 is sufficient to push the gripping jaws 2 and 3 apart.

The gripping jaws 2 and 3 can also be connected by a chain of sufficient length or a flexible plastic strip, so that the gripping jaws 2 and 3 cannot be separated and get lost.

The retaining device 1 can be made completely of strong plastic. To allow the retaining device 1 to be used in magnetic resonance tomography, the use of magnetic materials can be avoided.

The outsides of the retaining device 1 are as smooth as possible, to facilitate cleaning of the retaining device.

The retaining device 1 holds ventilation tubes 5 securely. Insertion of the ventilation tubes 5 and release of the ventilation tubes 5 can thereby be effected quickly and easily. The compact structure of the retaining device 1 means that the retaining device 1 is suitable in particular for use on X-ray examination tables. Use at bi-plane neuroradiology workstations should be considered particularly here. The lack of space there means that the compact structure of the retaining device 1 is particularly advantageous. Also a large proportion of anesthetized patients can be expected here.

The solid structure of the device 1, without small technical elements, is particularly advantageous in operating theaters, as the smooth, unstructured surfaces favor hygienic cleaning.

What is claimed is:

1. A holding device for a Medical breathing tube, comprising a clamp arranged in a predefined position relative to a body of a patient, the clamp having a first and second gripping jaw, and the clamp enclosing the breathing tube, wherein the first and second gripping jaws are adapted to clamp the breathing tube when interlocked, at least one of the first and second gripping jaws comprises a fixing device for fixing the gripping jaw to a stretcher, and the second gripping jaw engages in an opening of the first gripping jaw using an elongated element having a plurality of undercuts, the second gripping jaw secured in the opening by at least two mechanically non-coupling snapping devices, wherein the snapping device comprises a lock bar secured in the undercut using a spring.

2. The holding device according to claim 1 wherein pressure is forced upon the snapping device so that the clamping jaws are tightly fixed to the breathing tube using the undercut.

3. The holding device according to claim 1, wherein the elongated element is a toothed rack.

4. The holding device according to claim 1, further comprising a releasing device for releasing a tension of the spring.

5. The holding device according to claim 4, wherein the releasing device is manually operable.

6. The holding device according to claim 1, wherein at least two lock bars are each secured by a spring in an undercut assigned to each lock bar.

7. The holding device according to claim 6, wherein a tension of each spring is released by a releasing device.

8. The holding device according to claim 1, wherein an end of the elongated element projecting out of the opening is accommodated in a recess of a support holding the second gripping jaw.

9. The holding device according to claim 8, further comprising a spring secured in the recess for pushing out the elongated element.

* * * * *